US009606020B2

(12) United States Patent
Tamada et al.

(10) Patent No.: US 9,606,020 B2
(45) Date of Patent: *Mar. 28, 2017

(54) METHOD OF EVALUATING OPTICAL CHARACTERISTICS OF TRANSPARENT SUBSTRATE

(71) Applicant: ASAHI GLASS COMPANY, LIMITED, Tokyo (JP)

(72) Inventors: Minoru Tamada, Tokyo (JP); Yusuke Kobayashi, Tokyo (JP); Tomonobu Senoo, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 77 days.

This patent is subject to a terminal disclaimer.

(21) Appl. No.: 14/798,740

(22) Filed: Jul. 14, 2015

(65) Prior Publication Data
US 2015/0316442 A1 Nov. 5, 2015

Related U.S. Application Data

(63) Continuation of application No. PCT/JP2014/053219, filed on Feb. 12, 2014.

(30) Foreign Application Priority Data

Feb. 19, 2013 (JP) .................................. 2013-030238

(51) Int. Cl.
G01N 21/00 (2006.01)
G01M 11/00 (2006.01)
(Continued)

(52) U.S. Cl.
CPC ............. *G01M 11/00* (2013.01); *G01N 21/55* (2013.01); *G01N 21/4738* (2013.01);
(Continued)

(58) Field of Classification Search
CPC ... G01M 11/00; G01N 21/65; G01N 15/1459; G01J 3/02; G01J 3/51
See application file for complete search history.

(56) References Cited

U.S. PATENT DOCUMENTS

2007/0205706 A1* 9/2007 Yamada ................... G02B 1/10
313/110

FOREIGN PATENT DOCUMENTS

JP 09-189905 A 7/1997
JP 2007-147343 A 6/2007
(Continued)

OTHER PUBLICATIONS

International Search Report dated Apr. 8, 2014 in PCT/JP2014/053219, filed Feb. 12, 2014.
(Continued)

*Primary Examiner* — Abdullahi Nur
(74) *Attorney, Agent, or Firm* — Oblon, McClelland, Maier & Neustadt, L.L.P.

(57) ABSTRACT

The present invention is a method of evaluating optical characteristics of a transparent substrate that is disposed on a display device, wherein the optical characteristics of the transparent substrate are evaluated by selecting two values among a quantified resolution index value (T), a quantified reflection image diffusiveness index value (R), and a quantified sparkle index value of the transparent substrate. According to the present invention, a transparent substrate and an anti-glare process that is to be applied to it can be properly selected, depending on purpose and use. The present invention can be utilized, for example, for evaluating optical characteristics of a transparent substrate that is installed in various types of display devices, such as an LCD device, an OLED device, a PDP device, and a tablet type display device.

20 Claims, 12 Drawing Sheets

(51) Int. Cl.
    *G01N 21/55*     (2014.01)
    *G01N 21/47*     (2006.01)
    *G01N 21/57*     (2006.01)
    *G02F 1/1335*     (2006.01)

(52) U.S. Cl.
    CPC ....... *G01N 21/57* (2013.01); *G01N 2021/555* (2013.01); *G01N 2021/558* (2013.01); *G02F 1/133502* (2013.01)

(56) References Cited

FOREIGN PATENT DOCUMENTS

| | | |
|---|---|---|
| JP | 2008-197414 A | 8/2008 |
| JP | 2012-250861 A | 12/2012 |
| JP | 2012-250905 A | 12/2012 |

OTHER PUBLICATIONS

Yoshinori Uzuki, Seiichiro Hangai, "Subjective Evaluation of Images on LCDs with Different Resolution", 2004 Nen The Institute of Electronics, Information and Communication Engineers Sogo Taikai Koen Ronbunshu, Joho System (2), Mar. 8, 2004 (Mar. 8, 2004), p. 34.

Yoshio Itakura, "Kind of an optical film for FPD and a technical trend", Gekkan Display, Jun. 1, 2007 (Jun. 1, 2007), vol. 13, No. 6, pp. 2 to 14.

* cited by examiner

METHOD OF EVALUATING OPTICAL CHARACTERISTICS OF TRANSPARENT SUBSTRATE

CROSS-REFERENCE TO RELATED APPLICATION

The present application is a continuation application filed under 35 U.S.C. 111(a) claiming benefit under 35 U.S.C. 120 and 365(c) of PCT International Application No. PCT/JP2014/053219 filed on Feb. 12, 2014 and designating the U.S., which claims priority to Japanese Patent Application No. 2013-030238 filed on Feb. 19, 2013. The entire contents of the foregoing application are incorporated herein by reference.

BACKGROUND OF THE INVENTION

1. Field of the Invention

The present invention relates to a method of evaluating optical characteristics of a transparent substrate.

2. Description of the Related Art

In general, on a display device, such as a liquid crystal display (Liquid Crystal Display: LCD), a cover that is formed of a transparent substrate is disposed so as to protect the display device.

However, when such a transparent substrate is disposed on the display device, and when a displayed image of the display device is attempted to be viewed through the transparent substrate, often, an object that is disposed in the vicinity can be reflected. When such a reflection occurs on the transparent substrate, it may become difficult for a person viewing the displayed image to view the displayed image, and the person viewing the image may have an unpleasant impression.

Thus, for preventing such a reflection from occurring, for example, a method has been adopted that is for implementing an anti-glare process that is for forming an uneven shape on the surface of the transparent substrate.

Note that Patent Document 1 discloses a method of evaluating a reflection on the display device by using a special device.

Patent Document 1: Japanese Unexamined Patent Publication No. 2007-147343

As described above, Patent Document 1 shows the method of evaluating the reflection on the display device using the special device.

However, the optical characteristics that are required for a transparent substrate are not limited to reduction of the reflection. Namely, for a transparent substrate, depending on uses, various optical characteristics are required, such as a resolution, reflection image diffusiveness, and sparkle. Accordingly, for selecting a transparent substrate, it may be insufficient to consider only one of the optical characteristics. Often, there may arises a need to consider a plurality of optical characteristics at the same time.

The resolution that is described here is for representing whether and to what extent an image that matches a displayed image can be obtained when the displayed image is viewed through a transparent substrate. Further, the reflection image diffusiveness is for representing to what extent a reflected image of an object that (e.g., a light) is disposed in the vicinity of the transparent substrate matches the original object. Furthermore, the sparkle is for representing to what extent unevenness of a bright spot is observed that occurs when light (an image) from the display image passes through the transparent substrate, the light is reflected by the surface of the transparent substrate, and the scattered light beams mutually interfere.

Among the optical characteristics that are required for the transparent substrate, there are often characteristics that are in tradeoff relationships. For example, in general, in order to enhance the reflection image diffusiveness, the anti-glare process is applied to the surface of the transparent substrate. However, when such an anti-glare process is applied, a resolution of the transparent substrate tends to be lowered. In this manner, when the anti-glare process is to be applied to the transparent substrate based on a plurality of optical characteristics, it may become difficult to select a proper anti-glare process.

SUMMARY OF THE INVENTION

The present invention has been achieved in view of such a background. An object of the present invention is to provide a method of evaluating optical characteristics of a transparent substrate that can properly select a transparent substrate and an anti-glare process that is applied to it, depending on purpose and use.

According to the present invention, there is provided a method of evaluating optical characteristics of a transparent substrate that is disposed on a display device, wherein the optical characteristics of the transparent substrate are evaluated by selecting two values among a quantified resolution index value, a quantified reflection image diffusiveness index value, and a quantified sparkle index value of the transparent substrate.

In the method according to the present invention, a combination of the selected index values may be a combination of the resolution index value and the reflection image diffusiveness index value, a combination of the sparkle index value and the reflection image diffusiveness index value, or a combination of the resolution index value and the sparkle index value.

Further, in the method according to the present invention, the quantified resolution index value may be obtained by a step of irradiating a first light beam from a side of a second surface of the transparent substrate having a first surface and the second surface in a direction that is parallel to a thickness direction of the transparent substrate, and measuring brightness of a transmitted beam (which is referred to as "0° transmitted light beam") that is transmitted in a direction that is parallel to the thickness direction of the transparent substrate from the first surface, a step of varying a reception angle of the first light beam with respect to the first surface of the transparent substrate in a range from −90° to +90°, and measuring brightness of all the transmitted beams that are transmitted from a side of the first surface, and a step of calculating the resolution index value T from a following expression (1), wherein the resolution index value $T$=(the brightness of all the transmitted beams−the bright ness of the 0° transmitted light beam)/(the brightness of all the transmitted beams)    expression (1).

Further, in the method according to the present invention, the quantified reflection image diffusiveness index value may be obtained by a step of irradiating a second light beam from the side of the first surface of the transparent substrate having the first surface and the second surface in a direction that is 45° with respect to the thickness of the transparent substrate, and measuring brightness of a 45° regular reflected beam that is reflected on the first surface, a step of measuring brightness of all the reflected beams that are reflected by the first surface by varying a light reception angle of receiving the reflected beam that is reflected by the first surface in a range from 0° to +90°, and a step of calculating the reflection image diffusiveness index value R from a following expression (2), wherein the reflection image diffusiveness index value $R$=(the brightness of all the reflected beams−the brightness of the 45° regular reflected beam)/(the brightness of all the reflected beams)  expression (2).

Further, in the method according to the present invention, the resolution index value and/or the reflection image diffusiveness index value may be obtained by using a goniometer.

Further, in the method according to the present invention, the quantified sparkle index value is such that (a) disposing the transparent substrate that has the first surface and the second surface on the display device so that the second surface is a side of a display surface of the display device, (b) taking a photograph of the transparent substrate from the side of the first surface and obtaining a digital image, and (c) selecting a part of the digital image as an analysis area, dividing the analysis area into a plurality of areas that are formed of a plurality of pixels, obtaining, for each of the areas, the maximum brightness value and the maximum brightness gradient, and quantifying the sparkle of the transparent substrate by using an index value that is calculated from variations of the maximum brightness values and the maximum brightness gradients, respectively, in the analysis area.

Further, in the method according to the present invention, the display device may be one device that is selected from a group that includes a liquid crystal display (LCD) device, an organic light-emitting diode (OLED) device, a plasma display panel (PDP) device, and a tablet type display device.

Further, in the method according to the present invention, the transparent substrate may be formed of soda-lime glass or aluminosilicate glass.

In this case, a chemically strengthening process may be applied to at least one of the first surface and the second surface of the transparent substrate.

Further, in the method according to the present invention, an anti-glare process may be applied to the first surface, the second surface, or both the surfaces of the transparent substrate.

In this case, the anti-glare process may be implemented by applying at least one processing method on the first surface of the transparent substrate, wherein the at least one processing method is selected from a group including a frost process, an etching process, a sandblast process, a lapping process, and a silica-coating process.

According to the present invention, a method of evaluating chemical properties of a transparent substrate can be provided with which a transparent substrate can be properly selected depending on purpose and use.

DESCRIPTION OF THE PREFERRED EMBODIMENTS

Figure 1:
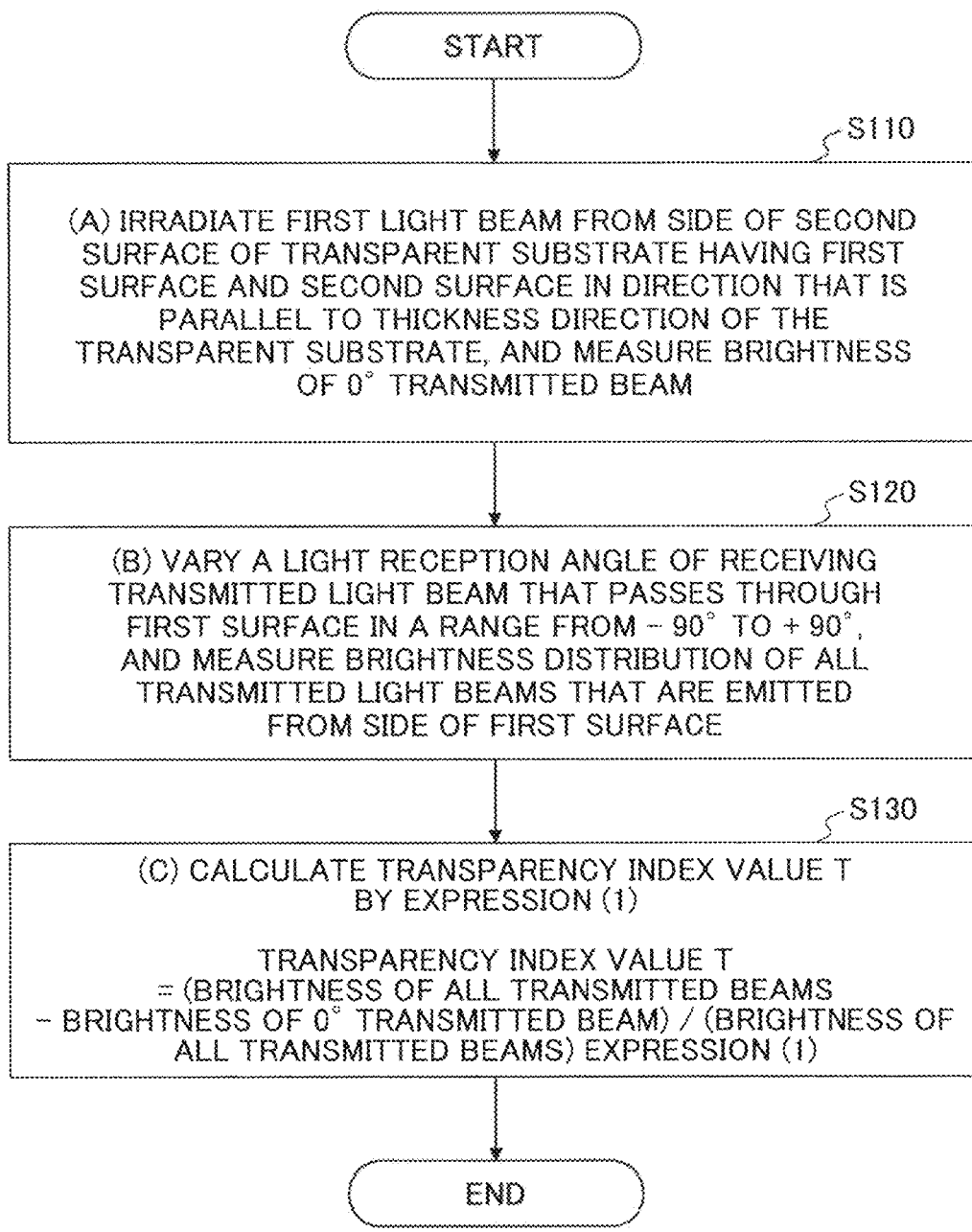
FIG. 1 is a diagram schematically showing a flow of a method of obtaining a resolution index value of a transparent substrate according to an embodiment of the present invention.

The present invention is explained in detail below.

In the present invention, there is provided a method of evaluating optical characteristics of a transparent substrate that is disposed on a display device. The method is characterized by evaluating the optical characteristics of the transparent substrate by selecting two index values among a resolution index value of the transparent substrate that is quantified, a reflection image diffusiveness index value of the transparent substrate that is quantified, and a sparkle index value of the transparent substrate that is quantified.

As described above, for a transparent substrate that is disposed on a surface of a display device, various optical characteristics are required, such as a resolution, reflection image diffusiveness, and an anti-glare property. Thus, for selecting a transparent substrate, there are often cases where it is insufficient to consider only a single optical property.

In contrast, according to the present invention, optical characteristics of a transparent substrate are evaluated by selecting two index values among the resolution index value, the reflection image diffusiveness index value, and the sparkle index value.

In such a method, a transparent substrate can be more properly selected because the transparent substrate can be selected by considering two optical characteristics.

Further, in the method according to the present invention, values that are expressed in numerical forms are used as the resolution index value, the reflection image diffusiveness index value, and the sparkle index value of the transparent substrate. Consequently, the optical characteristics of the resolution, the reflection image diffusiveness, and the sparkle can be objectively and quantitatively determined without depending on a subjective view and prejudice of an observer.

Furthermore, among the optical characteristics that are required for the transparent substrate, there are often optical characteristics that are in tradeoff relationships, such as the resolution and the reflection image diffusiveness. According to related art, in such a case, since there is no index that can be a basis for the selection, it has been difficult to properly select a transparent substrate with which both optical characteristics are satisfied.

However, in the method according to the present invention, two optical characteristics of a transparent substrate can be comprehensively and quantitatively evaluated. Thus, in the method according to the present invention, a transparent substrate that has the optimum optical characteristics can be properly selected depending on a purpose and a use.

Hereinafter, an embodiment of a method of obtaining a resolution index value, a reflection image diffusiveness index value, and a sparkle index value of a transparent substrate, which can be used in the method according to the present invention, is explained by referring to the drawings.

(Regarding the Resolution Index Value)

FIG. 1 schematically shows a flow of a method of obtaining a resolution index value of a transparent substrate according to an embodiment of the present invention.

As shown in FIG. 1, the method of obtaining the resolution index value of the transparent substrate includes (a) a step of irradiating a first light beam from a side of a second surface of the transparent substrate having a first surface and the second surface in a direction that is parallel to a thickness direction of the transparent substrate, and measuring brightness of a transmitted beam (which is also referred to as "0° transmitted light beam," hereinafter) that is transmitted in a direction that is parallel to the thickness direction of the transparent substrate from the first surface (step S110), (b) a step of varying a light reception angle for receiving the first light beam with respect to a thickness direction of the transparent substrate in a range from −90° to +90°, and measuring brightness of the first light beam (which is also referred to as "all the transmitted beams," hereinafter) that passes through the transparent substrate and that is emitted from the first surface (step S120), and (c) a step of calculating a resolution index value T by the following expression (1) (step S130):

the resolution index value $T$=(the brightness of all the transmitted beams−the brightness of the 0° transmitted light beam)/(the brightness of all the transmitted beams)    expression (1).

Hereinafter, each of the steps is explained.

(Step S110)

First, a transparent substrate is prepared that has a first surface and a second surface that face each other.

The transparent substrate may be formed of any material, provided that it is transparent. The transparent substrate may be glass or plastic, for example.

When the transparent substrate is formed of glass, compositions of the glass are not particularly limited. For example, the glass may be soda-lime glass or aluminosilicate glass.

Further, when the transparent substrate is formed of glass, a chemically strengthening process may be applied to the first surface and/or the second surface.

Here, the chemically strengthening process is said to be a general term of a technique for replacing an alkali metal (ions) having a small ionic radius that exists on an outermost surface of the glass substrate with an alkali metal (ions) having a large ionic radius that exists in a dissolved salt by immersing a glass substrate in the dissolved salt that includes the alkali metals. In the chemically strengthening process, an alkali metal (ions) having an ionic radius that is greater than that of the original atom is disposed on the surface of the processed glass substrate. Thus, compressive stress can be provided on the surface of the glass substrate, thereby enhancing the strength of the glass substrate (especially, break strength).

For example, when the glass substrate includes a sodium ion (Na+), this sodium ion is replaced with a potassium ion (Ka+) by the chemically strengthening process. Alternatively, for example, when the glass substrate include a lithium ion (Li+), this lithium ion may be replaced with a sodium ion (Na+) and/or a potassium ion (Ka+) by the chemically strengthening process.

When the transparent substrate is formed of plastic, compositions of the plastic are not particularly limited. For example, the transparent substrate may be a polycarbonate substrate.

Note that, prior to step S110, a step of applying an anti-glare process to the first surface of the transparent substrate may be implemented. The method of the anti-glare process is not particularly limited. For example, the anti-glare process may be a frost process, an etching process, a sandblast process, a lapping process, or a silica-coating process.

After the application of the anti-glare process, the first surface of the transparent substrate may have a surface roughness (an arithmetic average roughness Ra) in a range from 0.05 μm to 0.5 μm, for example.

Next, a first light beam is irradiated from a side of the second surface of the transparent substrate in a direction that is parallel to a thickness direction of the transparent substrate, specifically, in a direction of an angle θ=0°±0.5° (which is also referred to as a "direction of the angle 0°", hereinafter). The first light beam passes through the transparent substrate, and the first light beam is emitted from the first surface. The 0° transmitted light beam that is emitted in the direction of the angle 0° from the first surface is received, and its brightness is measured. It is referred to as the "brightness of the 0° transmitted light beam."

(Step S120)

Next, an angle θ of receiving the light beam that is emitted from the first surface is varied in a range from −90° to +90°, and a similar operation is executed. In this manner, a brightness distribution of the light beam that passes through the transparent substrate and that is emitted from the first surface is measured and summed, thereby defining the "brightness of all the transmitted light beams."

(Step S130)

Next, the resolution index value T is calculated from the following expression (1):

the resolution index value $T$=(the brightness of all the transmitted light beams−the brightness of the 0° transmitted light beam)/(the brightness of all the transmitted light beams)   expression (1).

As described below, it has been verified that the resolution index value T correlates with a determination result of the resolution by visual observation of an observer, and that it behaves like a human visual sense. For example, for a transparent substrate whose resolution index value T indicates a large value (close to 1), the resolution is unfavorable, and conversely, for a transparent substrate whose resolution index value T indicates a small value, the resolution is favorable. Accordingly, this resolution index value T can be used as a quantitative index for determining a resolution of a transparent substrate.

Figure 2:
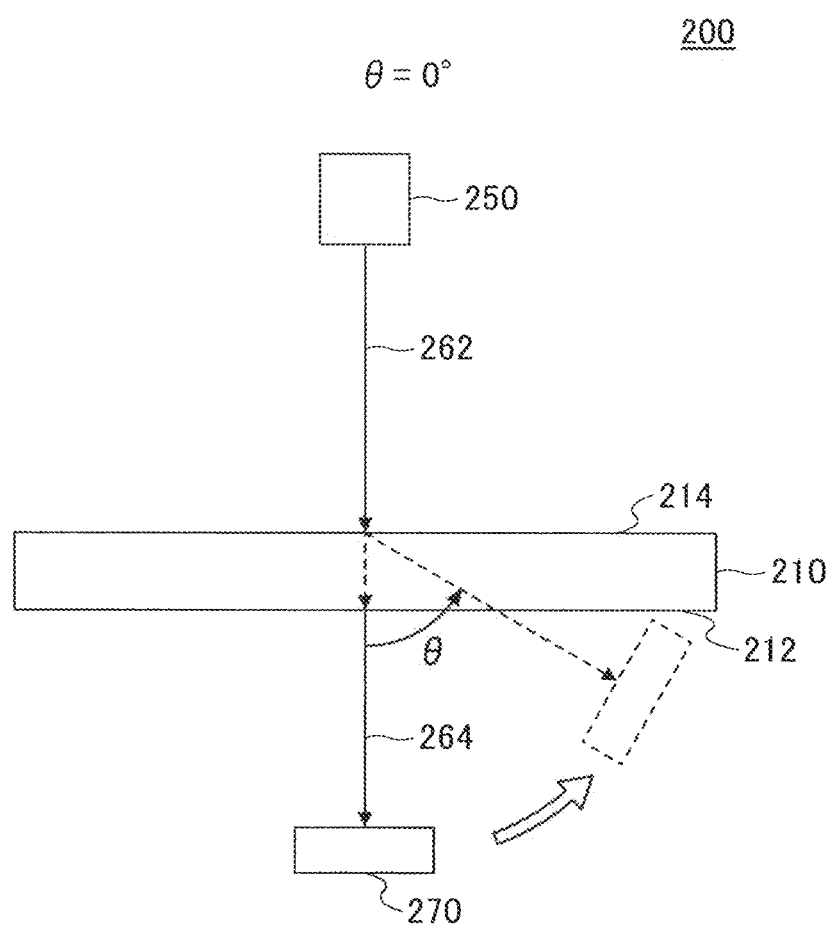
FIG. 2 is a diagram schematically showing an example of a measurement device that is used for obtaining the resolution index value.

FIG. 2 schematically shows an example of a measurement device that is used for obtaining the resolution index value T that is represented by the above-described expression (1).

As shown in FIG. 2, the measurement device 200 includes a light source 250; and a detector 270. A transparent substrate 210 is disposed in the measurement device 200. The transparent substrate 210 has a first surface 212 and a second surface 214. The light source 250 emits a first light beam 262 toward the transparent substrate 210. The detector 270 receives a transmitted light beam 264 that is emitted from the first surface 212, and detects its brightness.

Note that the transparent substrate 210 is arranged such that the second surface 214 is at the side of the light source 250, and the first surface 212 is at the side of the detector 270. Thus, the first light beam that is to be detected by the detector 270 is the transmitted light beam 264 that passes through the transparent substrate 210. Note that, when an anti-glare process is applied to one of the surfaces of the transparent substrate 210, the surface to which the anti-glare process is applied is the first surface 212 of the transparent substrate 210. Namely, in this case, the transparent substrate 210 is arranged in the measurement device 200, so that the surface to which the anti-glare process is applied is at the side of the detector 270.

Further, the first light beam 262 is irradiated at an angle θ that is parallel to the thickness direction of the transparent substrate 210. Hereinafter, this angle is defined to be 0°. Note that, in this application, by considering an error of the measurement device, the range of θ=0°±0.5° is defined to be the angle 0°.

In such a measurement device 200, the first light beam 262 is irradiated from the light source 250 toward the transparent substrate 210, and the transmitted light beam 264 that is emitted from the side of the first surface 212 of the transparent substrate 210 is detected by using the detector 270. In this manner, the 0° transmitted light beam is detected.

Next, the angle θ at which the detector 270 receives the transmitted light beam 264 is varied in a range from −90° to +90°, and the similar operation is executed.

In this manner, by using the detector 270, the transmitted light beam 264 that passes through the transparent substrate 210 and that is emitted from the first surface 212 is detected in the range from −90° to +90°, namely, all the transmitted light beams are detected.

From the obtained brightness of the 0° transmitted light beam and the obtained brightness of all the transmitted light beams, the resolution index value T of the transparent substrate 210 can be obtained by the above-described expression (1).

Note that such a measurement can be easily implemented by using a commercially available goniometer (a goniophotometer).

(Regarding the Reflection Image Diffusiveness Index Value)

Figure 3:
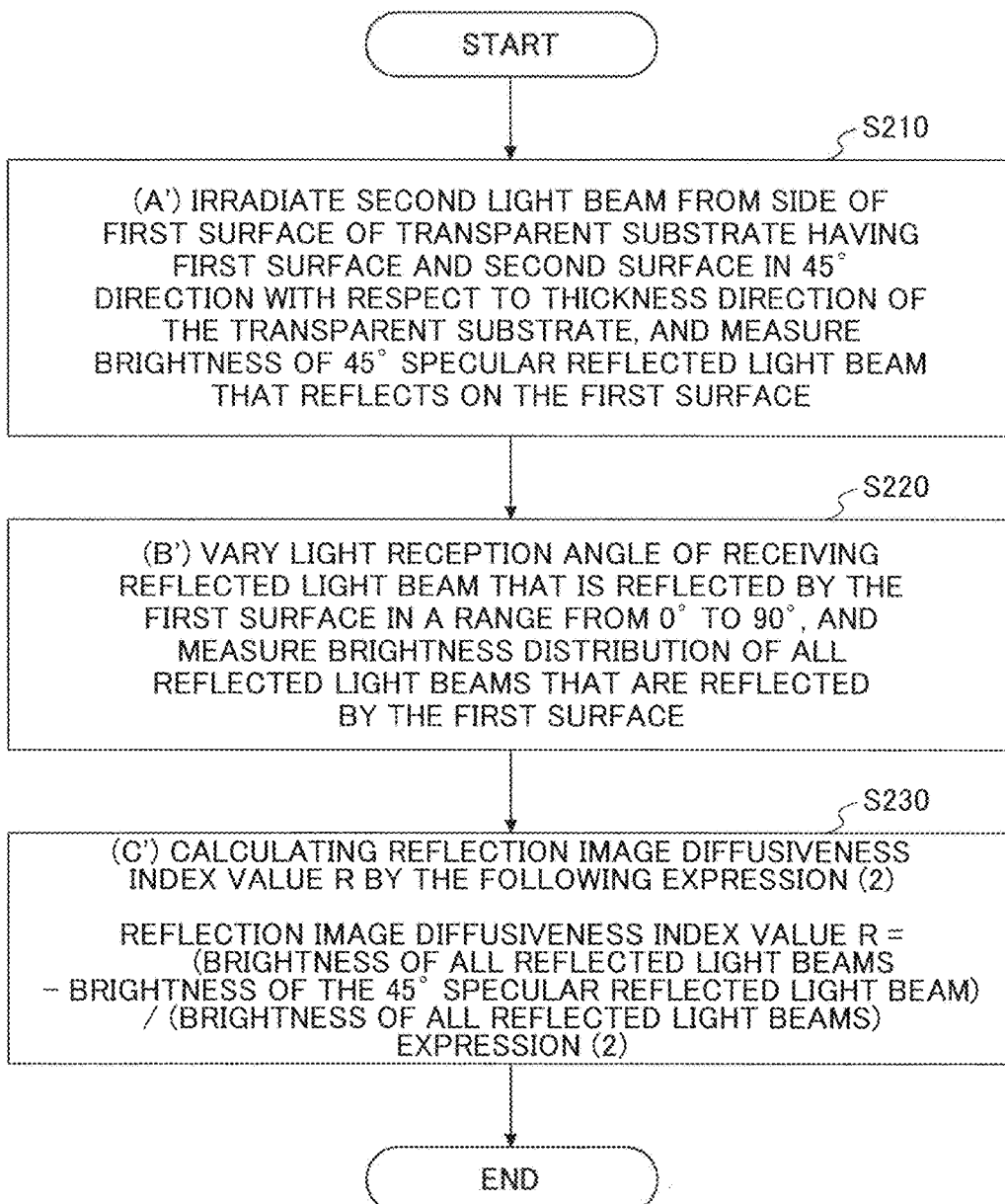
FIG. 3 is a diagram schematically showing a flow of a method of obtaining a reflection image diffusiveness index value of the transparent substrate according to the embodiment of the present invention.

FIG. 3 schematically shows a flow of a method of obtaining a reflection image diffusiveness index value of a transparent substrate, according to an embodiment of the present invention.

As shown in FIG. 3, the method of obtaining a reflection image diffusiveness index value of a transparent substrate includes (a') a step of irradiating a second light beam from a side of a first surface of the transparent substrate having the first surface and a second surface in a 45° direction with respect to a thickness direction of the transparent substrate, and measuring brightness of the light beam that is specularly reflected by the first surface (which is also referred to as the "45° specular reflected light beam," hereinafter) (step S210), (b') a step of varying a light reception angle for receiving the light beam that is reflected by the first surface in a range from 0° to 90°, and measuring brightness of the second light beam that is reflected by the first surface (which is also referred to as "all the reflected light beams," hereinafter) (step S220), and (c') a step of calculating the reflection image diffusiveness index value R by the following expression (2) (step S230):

the reflection image diffusiveness index value $R$=(the brightness of all the reflected light beams−the brightness of the 45° specular reflected light beam)/(the brightness of all the reflected light beams)   expression (2).

Hereinafter, each of the steps is explained.

(Step S210)

First, a transparent substrate is prepared that has a first surface and a second surface that face each other.

Since a material and composition of the transparent substrate are the same as those of step S110 that are described above, they are not explained here.

Next, the second light beam is irradiated from the side of the first surface of the prepared transparent substrate in a direction of 45°±0.5° with respect to the thickness direction of the transparent substrate. The second light beam is specularly reflected by the first surface of the transparent substrate. Among the reflected light beams, the 45° specular reflected light beam is received, its brightness is measured, and thereby the "brightness of the 45° specular reflected light beam" is defined.

(Step S220)

Next, the light reception angle of the reflected light beam that is reflected by the first surface is varied in a range from 0° to 90°, and the same operation is executed. At this time, a brightness distribution of the brightness of the second light beam that is reflected by the first surface of the transparent substrate and that is emitted from the first surface is measured and summed, and thereby the "brightness of all the reflected light beams" is defined.

(Step S230)

Next, the reflection image diffusiveness index value R is calculated by the following formula (2):

the reflection image diffusiveness index value $R$=(the brightness of all the reflected light beams−the brightness of 45° specular reflected light beam)/(the brightness of all the reflected light beams)   expression (2).

As described below, it has been verified that the reflection image diffusiveness index value R correlates with a determination result of the reflection image diffusiveness by visual observation of an observer, and that it behaves like a human visual sense. For example, for a transparent substrate whose reflection image diffusiveness index value R indicates a large value (close to 1), the reflection image diffusiveness is favorable, and conversely, for a transparent substrate whose reflection image diffusiveness index value R indicates a small value, the reflection image diffusiveness is unfavorable. Accordingly, this reflection image diffusiveness index value R can be used as a quantitative index for determining reflection image diffusiveness of a transparent substrate.

Figure 4:
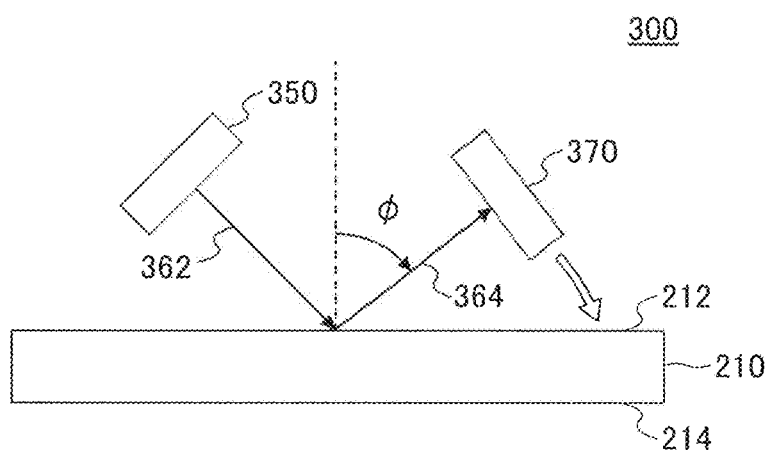
FIG. 4 is a diagram schematically showing an example of a measurement device that is used for obtaining the reflection image diffusiveness index value.

FIG. 4 schematically shows an example of a measurement device that is used for obtaining the reflection image diffusiveness index value R that is represented by the above-described expression (2).

As shown in FIG. 4, the measurement device 300 includes a light source 350, and a detector 370. The transparent substrate 210 is disposed in the measurement device 300. The transparent substrate 210 has the first surface 212 and the second surface 214. The light source 350 emits a second light beam 362 toward the transparent substrate 210. The detector 370 receives a reflected light beam 364 that is reflected by the first surface 212, and measures its brightness.

Note that the transparent substrate 210 is arranged such that the first surface 212 is at the side of the light source 350 and the detector 370. Thus, the second light beam that is detected by the detector 370 is the reflected light beam 364 that is reflected by the transparent substrate 210. Further, when an anti-glare process is applied to one of the surfaces of the transparent substrate 210, the surface to which the anti-glare process is applied is the first surface 212 of the transparent substrate 210. Namely, in this case, the transparent substrate 210 is arranged in the measurement device 300, so that the surface to which the anti-glare process is applied is at the side of the light source 350 and the detector 370.

Further, the second light beam 362 is irradiated at an angle that is tilted by 45° with respect to the thickness direction of the transparent substrate 210. Note that, in the present application, by considering an error of the measurement device, a range of 45°±0.5° is defined to be the angle of 45°.

In such a measurement device 300, the second light beam 362 is emitted from the light source 350 toward the transparent substrate 210, and the reflected light beam 364 that is reflected by the first surface 212 of the transparent substrate 210 is detected by using the detector 370. In this manner, the "45° specular reflected light beam" is detected.

Next, an angle $\phi$ at which the detector 370 measures the reflected light beam 364 is varied in a range from 0° to +90°, and the same operation is executed.

At this time, the reflected light beam 364 that is reflected by the first surface 212 of the transparent substrate 210 in the range from 0° to +90°, namely, a brightness distribution of all the reflected light beams is detected and summed by using the detector 370.

From the obtained brightness of the 45° specular reflected light beam and the obtained brightness of all the reflected light beams, the reflection image diffusiveness index value R of the transparent substrate 210 can be obtained by the above-described expression (2). Note that such a measurement can be easily implemented by using a commercially available goniometer (a goniophotometer).

(Regarding the Sparkle Index Value)

Figure 5:
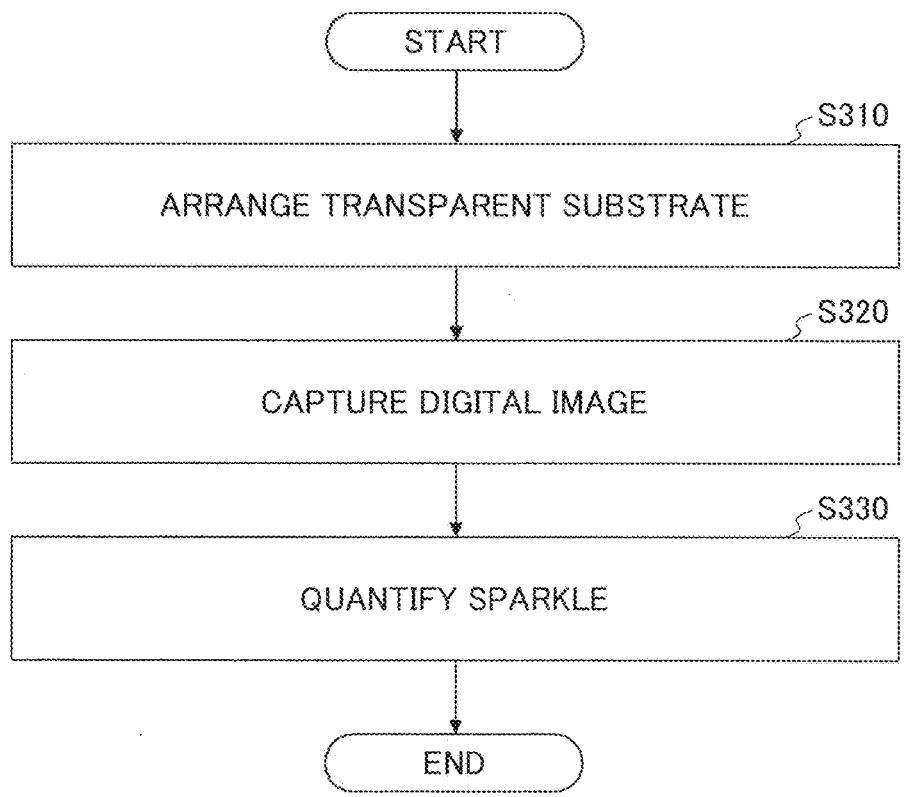
FIG. 5 is a diagram schematically showing a flow of a method of obtaining a sparkle index value of the transparent substrate according to the embodiment of the present invention.

FIG. 5 schematically shows a flow of a method of obtaining a sparkle index value of a transparent substrate, according to an embodiment of the present invention.

As shown in FIG. 5, the method of obtaining a sparkle index value of a transparent substrate includes (a") disposing the transparent substrate having a first surface and a second surface on a display device, so that the second surface is at a side of the display device (which is also referred to as "step S310: arrangement of the transparent substrate," hereinafter), (b") taking a photograph of the transparent substrate from the side of the first surface, and obtaining a digital image (which is also referred to as "step S320: obtainment of the digital image," hereinafter), and (c") selecting a part of the digital image as an analysis area, dividing the analysis area into a plurality of areas that are formed of a plurality of pixels, obtaining, for each of the areas, the maximum brightness value and the maximum brightness gradient, and quantifying the sparkle of the transparent substrate by using an index value that is calculated from variations of the maximum brightness values and the maximum brightness gradients, respectively, in the analysis area (which is also referred to as "step S330: quantification of the sparkle).

Hereinafter, each of the steps is explained in detail.

(Step 310)

First, a transparent substrate is prepared that has a first surface and a second surface that face each other.

Since a material and composition of the transparent substrate are the same as those of step S110 that are described above, they are not explained here.

Next, a display device is prepared. The display device is not particularly limited. For example, the display device may be a liquid crystal display (LCD) device, an organic light emitting diode (OLED) device, a plasma display panel (PDP) device, or a tablet type display device.

Next, the transparent substrate is disposed on the display device. At this time, the transparent substrate is disposed on the display device, so that the second surface is at the side of the display device.

(Step S320)

Next, a photograph of the transparent substrate is taken from the side of the first surface in a state in which the display device is turned on (i.e., a state in which an image is displayed), and an image of the transparent substrate that is disposed on the display device is obtained.

The image that is displayed on the display device may preferably be an image in a single color (e.g., green), and may preferably be displayed on the whole display screen of the display device. That is for minimizing an effect, such as a difference in appearance due to a difference in the displayed color.

For taking the photograph, a digital camera having a large pixel number (number of pixels) may preferably be used, from the perspective of enhancing the reproducibility of the measurement. For example, a CCD image sensor camera can be used. It may preferably have an area of an image sensor and a number of pixels that are sufficient for determining, at least, a size that is smaller than the surface unevenness of the transparent substrate after applying the anti-glare process and that is smaller than a pixel pitch. Additionally, it is desirable to fix a distance between a photodetector of the digital camera and a sample of which a photograph is to be taken because the reproducibility of the measurement can be enhanced.

An image of the transparent substrate that is captured is input into an analysis device (e.g., a computer).

(Step S330)

Next, a part of the digital image is selected as an analysis area, the analysis area is divided into a plurality of areas that are formed of a plurality of pixels, a maximum brightness value and a maximum brightness gradient are obtained for each of the areas, a quantified sparkle index value is calculated from variations of the maximum brightness values and the maximum brightness gradients, respectively, in the analysis area, and the value is defined to be the sparkle index value. The size of the analysis area can be freely selected, provided that it is in a range in which subsequent evaluation of the variation of the brightness values and the like can be executed, and an amount of calculation can be appropriate. For example, the analysis area can be a rectangular area that is in a range from 128 pixels×100 pixels to 256 pixels×200 pixels. Further, the analysis area is divided into a plurality of areas that are formed of a plurality of pixels, and the maximum brightness value and the maximum brightness gradient are obtained for each of the areas. Each of the areas may preferably have the same pixel numbers such that the analysis area can be filled by the areas without overlapping the areas, and may preferably have the pixel number that is suitable for obtaining the maximum brightness value and the brightness gradients. For example, it can be a rectangular area in a range from 4 pixels×4 pixels to 16 pixels×16 pixels.

The maximum brightness value is obtained from the maximum value of the brightness values of the pixels in each area. The maximum brightness gradient is obtained from the maximum value of differences between the brightness values of the adjacent pixels in each area. The quantified sparkle index value is calculated from a variation of the maximum brightness values and a variation of the maximum brightness gradients (e.g., standard deviations) in the analysis area. Such an analysis can be executed, for example, by using an ISC-A value that is output by Eyescale-4W (a product of I-System Co., Ltd.), which is a commercially available software product, as an index value.

As described below, it has been verified that the sparkle index value correlates with a determination result of the sparkle by visual observation of an observer, and that it behaves like a human visual sense. For example, for a transparent substrate whose sparkle index value is a large value, the sparkle tends to be significant, and conversely, for a transparent substrate whose sparkle index value is a small value, the sparkle tends to be suppressed. Accordingly, this sparkle index value can be used as a quantitative index for determining sparkle of a transparent substrate.

By using the above-described resolution index value T, the reflection image diffusiveness index value R, and the sparkle index value, optical characteristics of a transparent substrate can be quantitatively evaluated.

(Evaluation by Two Indexes)

Next, there are explained a method of simultaneously evaluating two optical characteristics of a transparent substrate and its effect.

Figure 6:
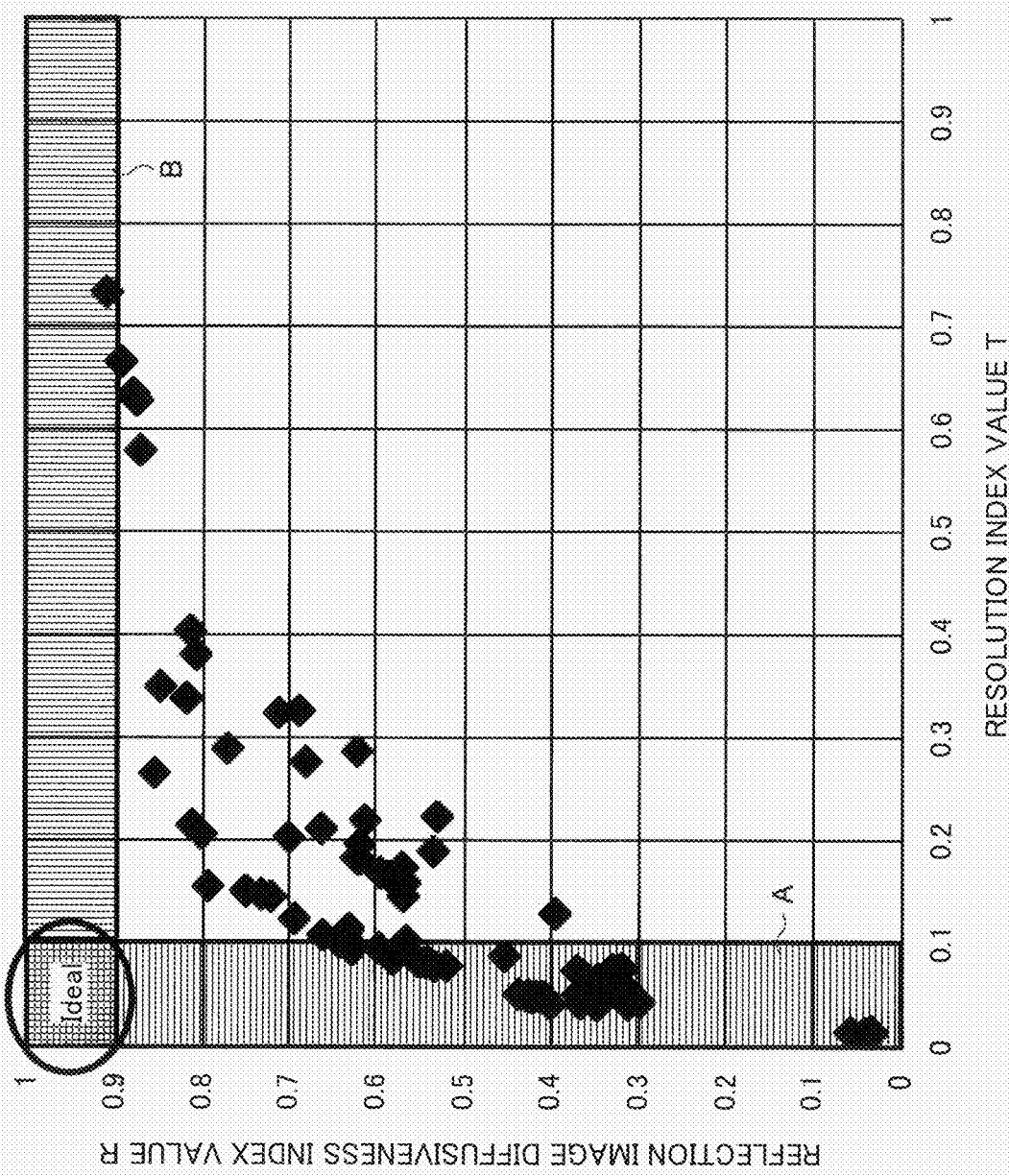
FIG. 6 is a diagram that is obtained by plotting an example of a relationship between the resolution index value T (a horizontal axis) and the reflection image diffusiveness index value (a vertical axis) that is obtained for each type of the transparent substrate.

When a resolution and reflection image diffusiveness of a transparent substrate are to be simultaneously evaluated, a correlation diagram that is shown in FIG. 6 can be used, for example.

FIG. 6 is a diagram that is obtained by plotting an example of a relationship between the resolution index value T (the horizontal axis) and the reflection image diffusiveness index value R (the vertical axis) that are obtained for various types of transparent substrates. In the figure, as the resolution index value T of the horizontal axis becomes smaller, the resolution of the transparent substrate is enhanced, and as the reflection image diffusiveness index value R of the vertical axis becomes greater, the reflection image diffusiveness of the transparent substrate is enhanced.

Note that, in FIG. 6, for reference, an ideal area of the transparent substrate that has both a favorable (high) resolution and favorable reflection image diffusiveness is indicated by a circle mark that is indicated as "Ideal."

Here, as before, when a candidate transparent substrate is to be selected among various types of transparent substrates by only considering a single optical characteristic, for example, by only considering the resolution, transparent substrates that are included in the area A that is indicated in FIG. 6 by the hatching are to be uniformly selected. Namely, with such a method, a transparent substrate whose reflection image diffusiveness is unfavorable may be included in the transparent substrates that are the candidates of the selection. Similarly, when a transparent substrate is to be selected by considering only the reflection image diffusiveness, transparent substrates that are included in the area B that is indicated in FIG. 6 by the hatching are to be uniformly selected, and a transparent substrate whose resolution is unfavorable may be included in the transparent substrates that are the candidates of the selection.

Further, as described above, the resolution and the reflection image diffusiveness are in a tradeoff relationship. Thus, it is substantially impossible to obtain a transparent substrate having both the characteristics, namely, to obtain a transparent substrate that exists in the area that is indicated by the circle mark. Consequently, a proper transparent substrate may not be selected only by separately considering the resolution and the reflection image diffusiveness.

In contrast, when the correlation diagram of the resolution index value T and the reflection image diffusiveness index value R, such as shown in FIG. 6, is used, a proper transparent substrate can be selected by simultaneously considering both the optical characteristics. Namely, in such a selection method, a transparent substrate can be properly selected, depending on purpose and use. Namely, with respect to the resolution and the reflection image diffusiveness, a transparent substrate can be selected, so that the most favorable characteristics can be achieved.

Figure 7:
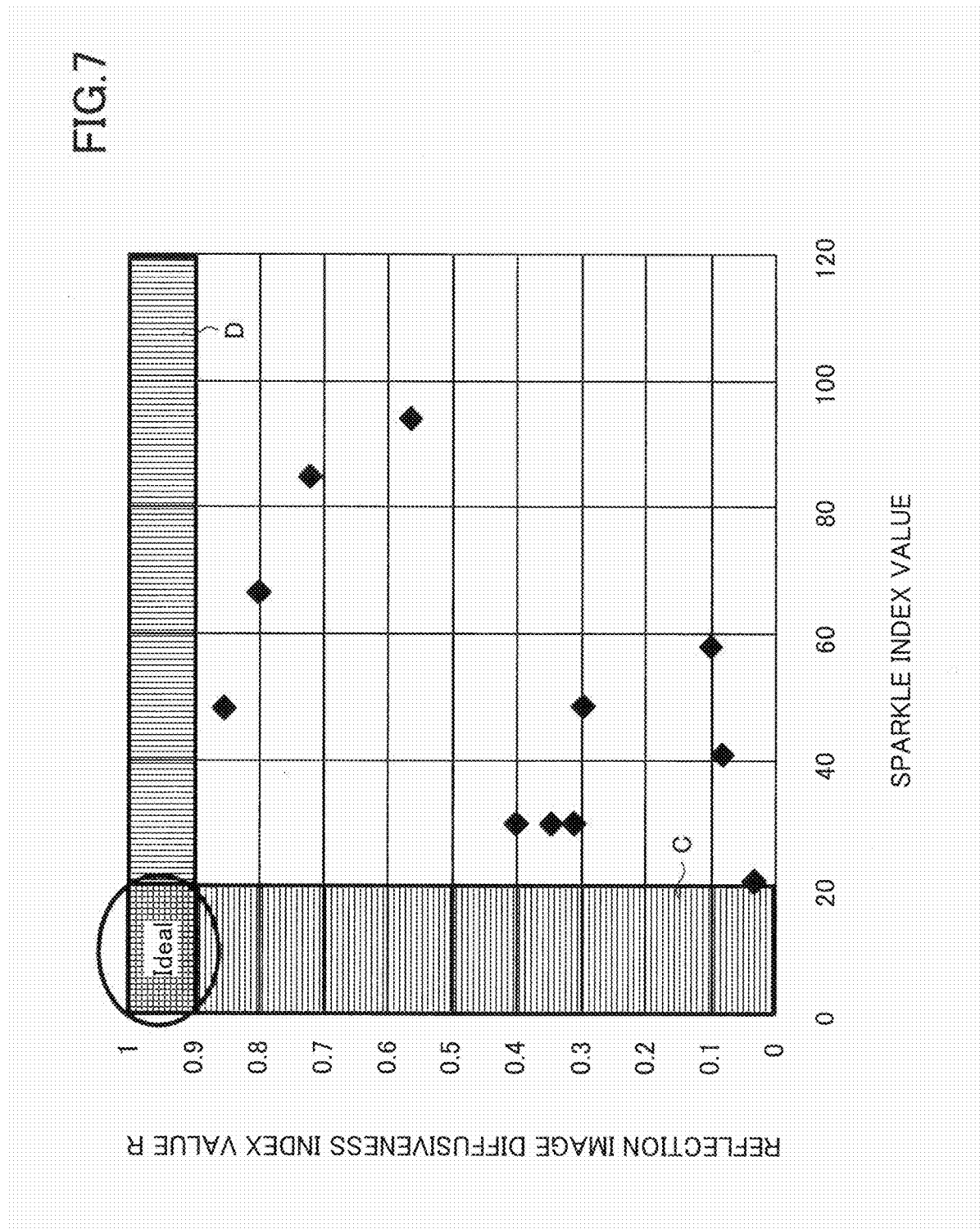
FIG. 7 is a diagram that is obtained by plotting an example of a relationship between the sparkle index value (a horizontal axis) and the reflection image diffusiveness index value (a vertical axis) that is obtained for each type of the transparent substrate.

Next, FIG. 7 shows a diagram that is obtained by plotting an example of a relationship between the sparkle index value (the horizontal axis) and the reflection image diffusiveness index value R (the vertical axis) that is obtained for various types of transparent substrates. In the figure, as the sparkle index value of the horizontal axis becomes smaller, the sparkle of the transparent substrate is suppressed, and as the reflection image diffusiveness index value R of the vertical axis becomes greater, the reflection image diffusiveness of the transparent substrate is enhanced.

Note that, in FIG. 7, for reference, an ideal area of the transparent substrate that has both a favorable anti-glare property and favorable reflection image diffusiveness is indicated by a circle mark that is indicated as "Ideal."

For the case of the anti-glare property and the reflection image diffusiveness, when a candidate transparent substrate is to be selected among various types of transparent substrates by considering a single optical property, for example, by only considering the anti-glare property, as before, the transparent substrates that are included in the area C that is indicated in FIG. 7 by the hatching are to be uniformly selected. Namely, with such a method, a transparent substrate having unfavorable reflection image diffusiveness is to be included in the transparent substrates that are the candidates of the selection. Similarly, when a transparent substrate is to be selected by only considering the reflection image diffusiveness, the transparent substrates that are included in the area D that is indicated in FIG. 7 by the hatching are to be uniformly selected, and a transparent substrate having an unfavorable anti-glare property is to be included in the transparent substrates that are the candidates of the selection.

Further, for the anti-glare property and the reflection image diffusiveness, it is difficult to optimize both the characteristics, and it is substantially impossible to obtain a transparent substrate such that both the characteristics exist in the ideal area that is indicated by the circle mark. Consequently, a proper transparent substrate may not be selected only by separately considering the anti-glare property and the reflection image diffusiveness.

In contrast, when the correlation diagram of the sparkle index value and the reflection image diffusiveness index value R, such as shown in FIG. 7, is used, a proper transparent substrate can be selected by simultaneously considering both the optical characteristics. Namely, in such a selection method, a transparent substrate can be properly selected, depending on purpose and use. Namely, with respect to the anti-glare property and the reflection image diffusiveness, a transparent substrate can be selected, so that the most favorable characteristics are achieved.

Figure 8:
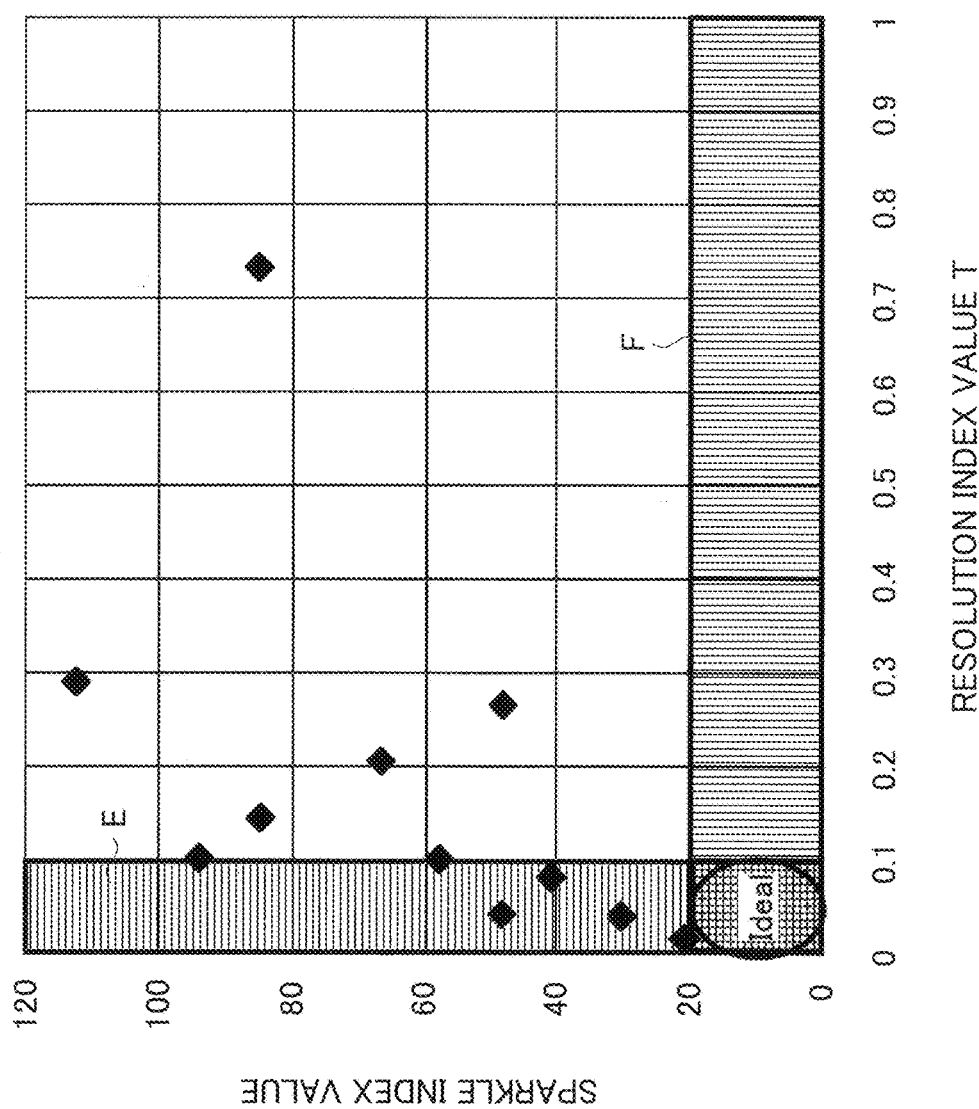
FIG. 8 is a diagram that is obtained by plotting an example of a relationship between the resolution index value (a horizontal axis) and the sparkle index value (a vertical axis) that is obtained for each type of the transparent substrate.

Next, FIG. 8 shows a diagram that is obtained by plotting an example of a relationship between the resolution index value T (the horizontal axis) and the sparkle index value (the vertical axis) that is obtained for various types of transparent substrates. In FIG. 8, as the resolution index value T of the horizontal axis becomes smaller, the resolution of the transparent substrate is enhanced, and as the sparkle index value of the vertical axis becomes smaller, the sparkle of the transparent substrate is suppressed (i.e., the anti-glare property is enhanced).

Note that, in FIG. 8, for reference, an ideal area of the transparent substrate that has both a favorable resolution and a favorable anti-glare property is indicated by a circle mark that is indicated as "Ideal."

For the case of the resolution and the anti-glare property, when a candidate transparent substrate is to be selected among various types of transparent substrates by considering a single optical property, for example, by only considering the resolution, as before, the transparent substrates that are included in the area E that is indicated in FIG. 8 by the hatching are to be uniformly selected. Namely, with such a method, a transparent substrate having an unfavorable anti-glare property is to be included in the transparent substrates that are the candidates of the selection. Similarly, when a transparent substrate is to be selected by only considering the anti-glare property, the transparent substrates that are included in the area F that is indicated in FIG. 8 by the hatching are to be uniformly selected, and a transparent substrate having an unfavorable resolution is to be included in the transparent substrates that are the candidates of the selection.

In contrast, when the correlation diagram of the resolution index value T and the sparkle index value, such as shown in FIG. 8, is used, a proper transparent substrate can be selected by simultaneously considering both the optical characteristics. Namely, in such a selection method, a transparent substrate can be properly selected, depending on purpose and use. Namely, with respect to the resolution and the anti-glare property, a transparent substrate can be selected, so that the most favorable characteristics can be achieved.

In this manner, in the method according to the embodiment of the present invention, a transparent substrate can be more properly selected, depending on purpose and use, because two optical characteristics can be quantitatively considered at the same time.

Further, in the method according to the present invention, values that are expressed in numerical forms are used as the resolution index value, the reflection image diffusiveness index value, and the sparkle index value. Consequently, the optical characteristics of the resolution, the reflection image diffusiveness, and the sparkle can be objectively and quantitatively determined without depending on a subjective view and prejudice of an observer.

Working Examples

Next, there are explained results of evaluation of a resolution, evaluation of reflection image diffusiveness, and evaluation of sparkle that were implemented by using an actual transparent substrate.

(Regarding the Evaluation of the Resolution)

Various types of transparent substrates were prepared, and these transparent substrates were evaluated by the following method.

First, transparent substrates were prepared whose first surfaces were anti-glare processed by corresponding various methods. Each of the transparent substrates were formed of glass. The thickness of the transparent substrates was selected in a range from 0.5 mm to 3.0 mm.

Further, a standard test chart that was formed of plastic (a high definition resolution chart I-type: produced by Dai Nippon Printing Co., Ltd.) was prepared.

Next, each transparent substrate was disposed above the standard test chart. At that time, each of the transparent substrates was arranged, so that a side of the first surface (i.e., the anti-glare processed surface) of the transparent substrate was at the opposite side of the standard test chart. Note that the space between each of the transparent substrates and the standard test chart was set to 1 cm.

Next, the standard test chart was visually observed through the transparent substrate, the limit of the bars that could be viewed (the number of TV lines) was evaluated. In this manner, a resolution level by visual observation was evaluated for each of the transparent substrates. Note that the maximum value of the TV lines of this standard test chart was 2000.

Next, by executing the operations such as shown in the above-described step S110 to step S130 by using a goniophotometer (GC5000L: produced by NIPPON DENSHOKU INDUSTRIES CO., LTD), the resolution index value T for each of the transparent substrates was calculated from the expression (1). Note that, at step S120, the range of the reception angle of the measurement device was from −85° to +85°, due to the constraints on the configuration as a measurement device. Since the transmitted light volumes from −90° to −85° and from +85° to +90° were almost zero, this measurement range did not cause any significant impact for calculating the resolution index value T.

Figure 9:
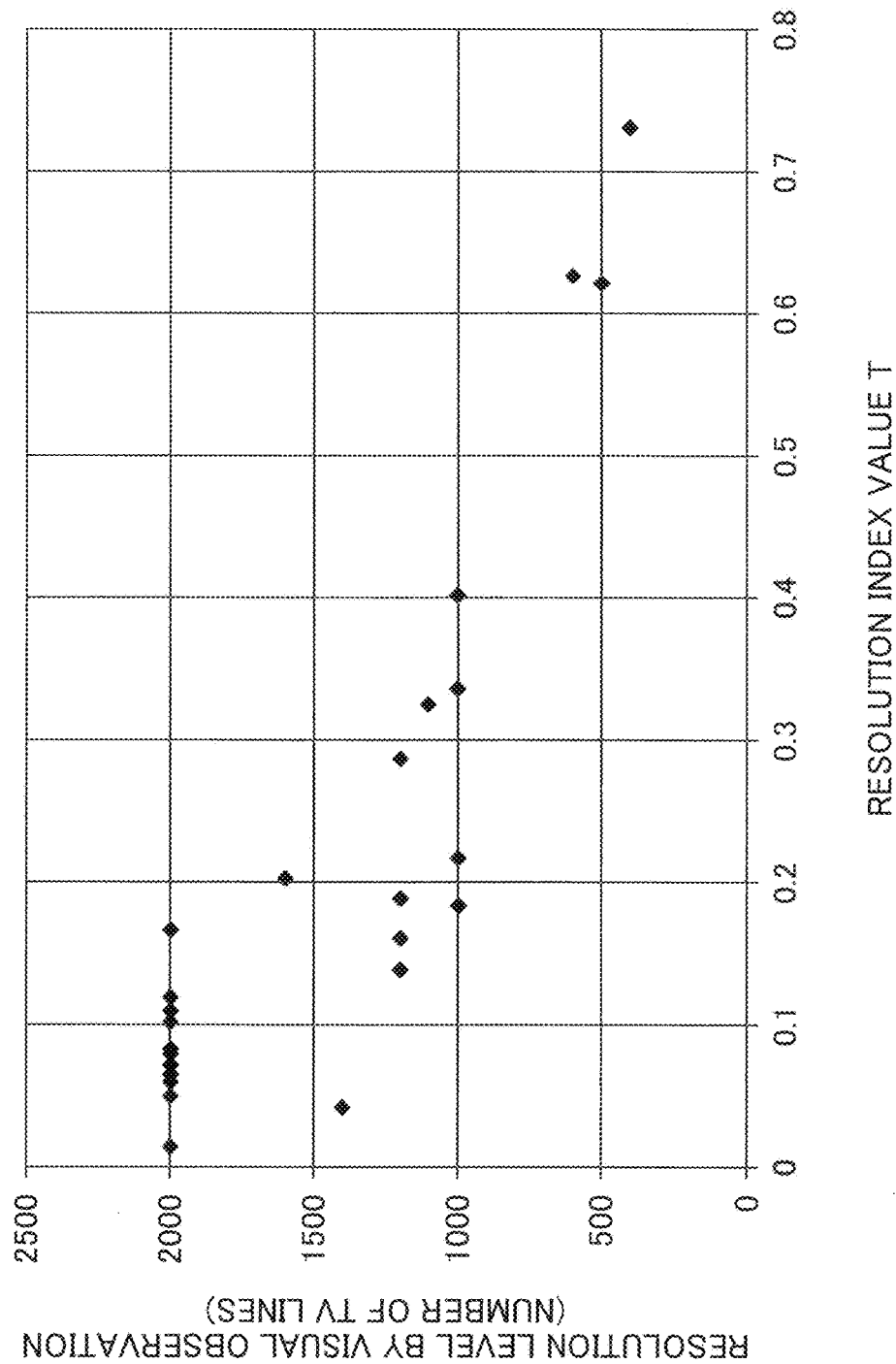
FIG. 9 is a graph that shows an example of a relationship between a determination result of a resolution level by a visual observation (a vertical axis) and the resolution index value T (a horizontal axis) that is obtained for each type of the transparent substrate.

FIG. 9 shows an example of a relationship between a result of determination of a resolution level by visual observation (the vertical axis) and a resolution index value T (the horizontal axis) that was obtained for each of the transparent substrates.

From FIG. 9, it can be seen that there is a negative correlation between them. Note that, in the vicinity of the resolution index value T of 0.1, there were several transparent substrates for which the resolution levels by the visual observation were saturated at the maximum value of 2000.

This result indicates that the resolution index value T corresponds to a tendency of the determination, by the observer, of the resolution by the visual observation, and therefore suggests that the resolution of the transparent substrate can be determined by using the resolution index value T. In other words, it can be said that, by using the resolution index value T, the resolution of the transparent substrate can be objectively and quantitatively determined.

(Regarding the Evaluation of the Reflection Image Diffusiveness)

Next, by using the above-described various transparent substrates that were used for the evaluation of the resolution, the reflection image diffusiveness of each of the transparent substrates was evaluated by the following method.

First, each of the transparent substrates was visually observed from the side of the first surface (i.e., the anti-glare processed surface), and the reflection image diffusiveness was evaluated in twelve levels that were from level 1 to level 12. Note that the direction of the observation was the direction of 45° with respect to the thickness direction of the transparent substrate.

Figure 10:
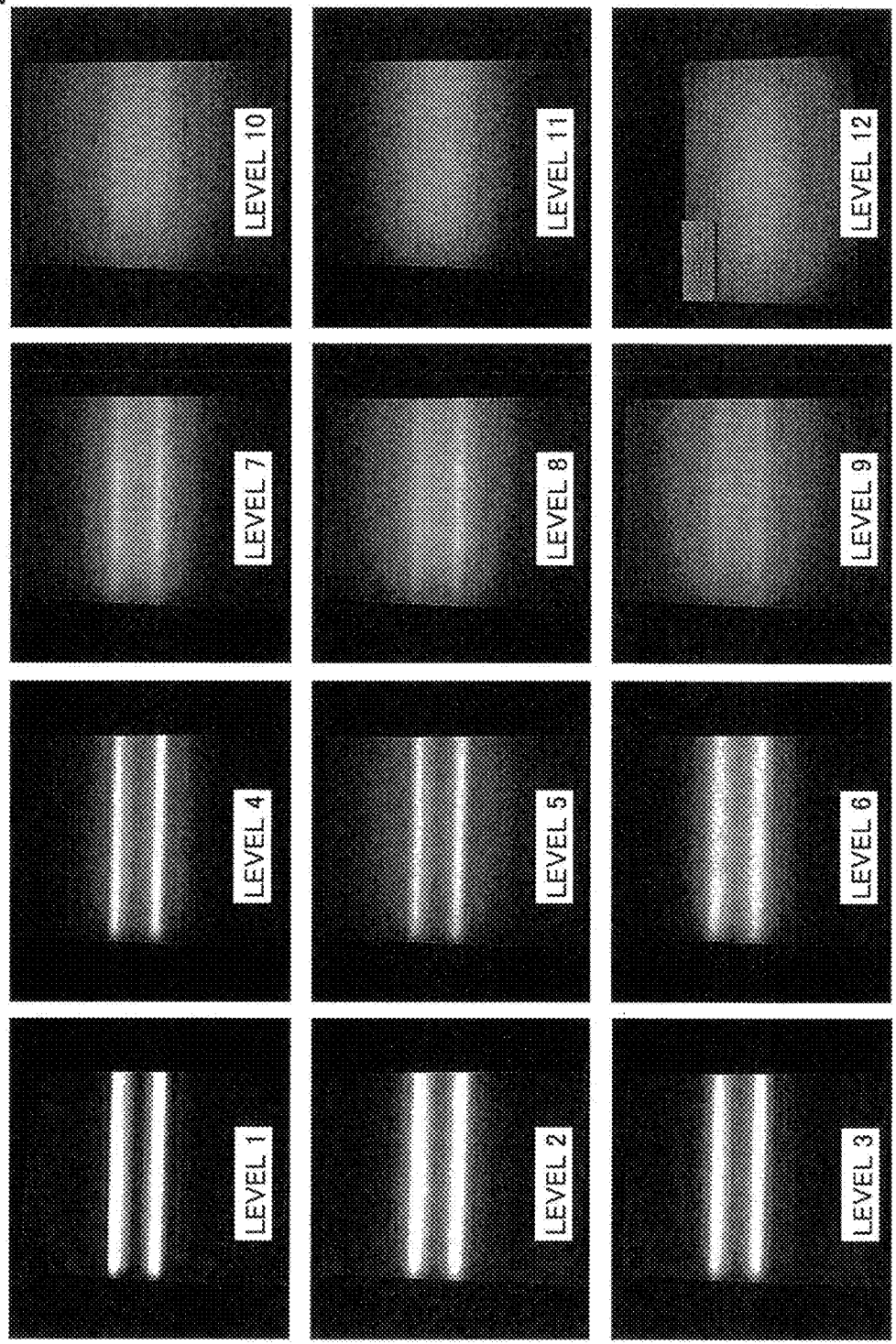
FIG. 10 is a diagram that collectively shows transparent substrates that have the reflection image diffusiveness index values from level 1 to level 12, respectively.

FIG. 10 collectively shows, for reference, examples of the reflection image diffusiveness that correspond to level 1 to level 12, respectively. Note that this figure is obtained by separately taking photographs of the transparent substrates that correspond to these levels, respectively.

From FIG. 10, it can be seen that, along with level 1 to level 12, the reflection image on the transparent substrate gradually becomes insignificant, namely, the reflection image diffusiveness of the transparent substrate tends to be enhanced. Note that the state of level 1 was obtained in the transparent substrate such that no anti-glare process was applied to each of its surfaces.

Next, by executing the operations such as shown in the above-described step S210 to step S230 by using a goniophotometer (GC5000L: produced by NIPPON DENSHOKU INDUSTRIES CO., LTD), the reflection image diffusiveness index value R for each of the transparent substrates was calculated from the expression (2). Note that, at step S220, a range of the reception angle of the measurement device was from +5° to +85°, due to the constraints on the configuration as a measurement device. Since the reflected light volumes from 0° to +5° and from +85° to +90° were almost zero, the measurement range did not cause any significant impact for calculating the reflection image diffusiveness index value R.

Figure 11:
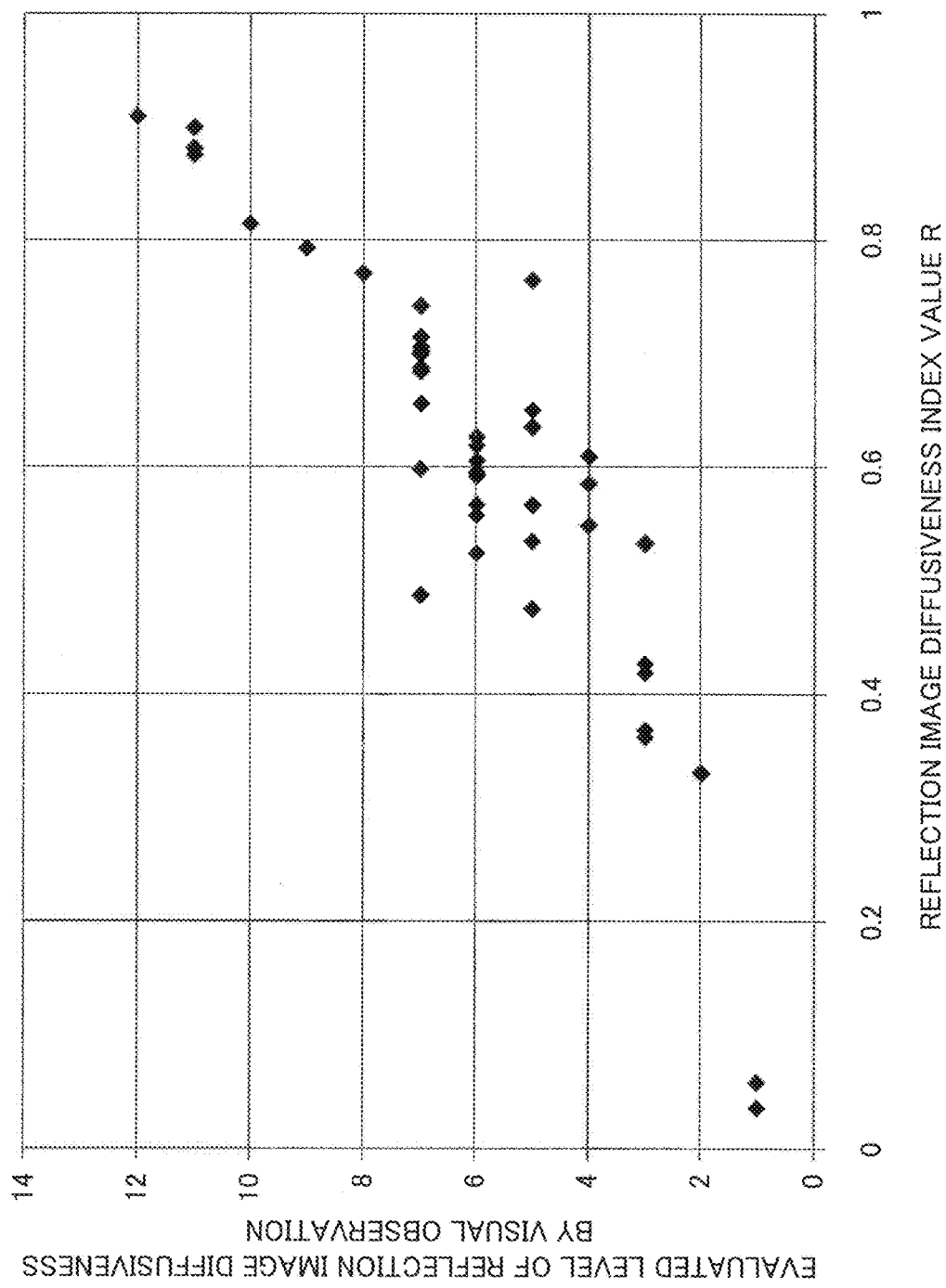
FIG. 11 is a graph showing an example of a relationship between a level of the reflection image diffusiveness index value by a visual observation (a vertical axis) and the reflection image diffusiveness index value R (a horizontal axis) that is obtained for each type of the transparent substrate.

FIG. 11 shows an example of a relationship between a level of the reflection image diffusiveness that was evaluated by visual observation (the vertical axis) and the reflection image diffusiveness index value R (the horizontal axis) that was obtained for each of the transparent substrates.

From FIG. 11, it can be seen that there is a positive correlation between them.

This result indicates that the reflection image diffusiveness index value R corresponds to a tendency of the evaluated level of the reflection image diffusiveness by the visual observation by the observer, and therefore suggests that the reflection image diffusiveness of the transparent substrate can be determined by using the reflection image diffusiveness index value R. In other words, it can be said that, by using the reflection image diffusiveness index value R, the reflection image diffusiveness of the transparent substrate can be objectively and quantitatively determined.

(Regarding the Evaluation of the Sparkle)

Next, by using the above-described various transparent substrates that were used for the evaluation of the resolution, the sparkle of each of the transparent substrates was evaluated by the following method.

First, each of the transparent substrates was directly disposed on a display device (iPhone 4S (registered trademark)). At that time, each of the transparent substrates was disposed on the display device, so that the first surface of each of the transparent substrates (i.e., the anti-glare processed surface) was at the side of the observer. Note that an image that was displayed on the display device was a single-color green image, and the size of the image was set to 7.5 cm×5.1 cm.

Next, in this state, each of the transparent substrates was visually observed from the side of the first surface, and the sparkle was evaluated in 11 levels that were from level 0 to level 10. Level 0 indicates that almost no sparkle can be observed, and level 10 indicates that the sparkle is extremely significant. Further, the values of the levels between them have tendency such that, as the value become greater, the sparkle becomes more significant.

Figure 12:
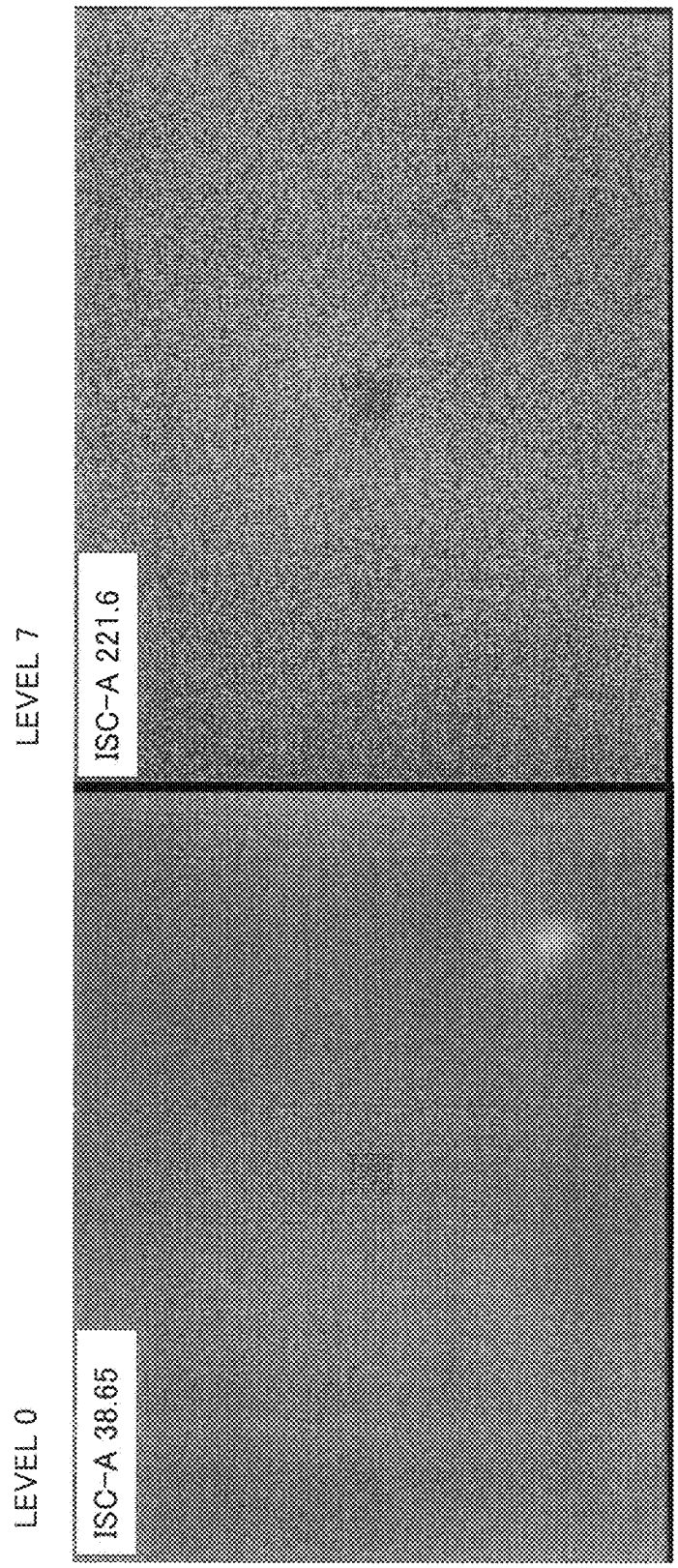
FIG. 12 is a diagram showing transparent substrates that indicate sparkle of level 0 and sparkle of level 7, respectively.

FIG. 12 shows, for reference, examples of the transparent substrates that indicate the sparkle of level 0 and the sparkle of level 7, respectively. Note that the level 0 was obtained for the transparent substrate such that no anti-glare process was applied to each of its surfaces.

Next, by executing the operations such as shown in the above-described step S320 to step S330, an ISC-A value of each of the transparent substrates was obtained by using the software Eyescale-4W (produced by I-System Co., Ltd.), and the sparkle index value was set to that value.

Figure 13:
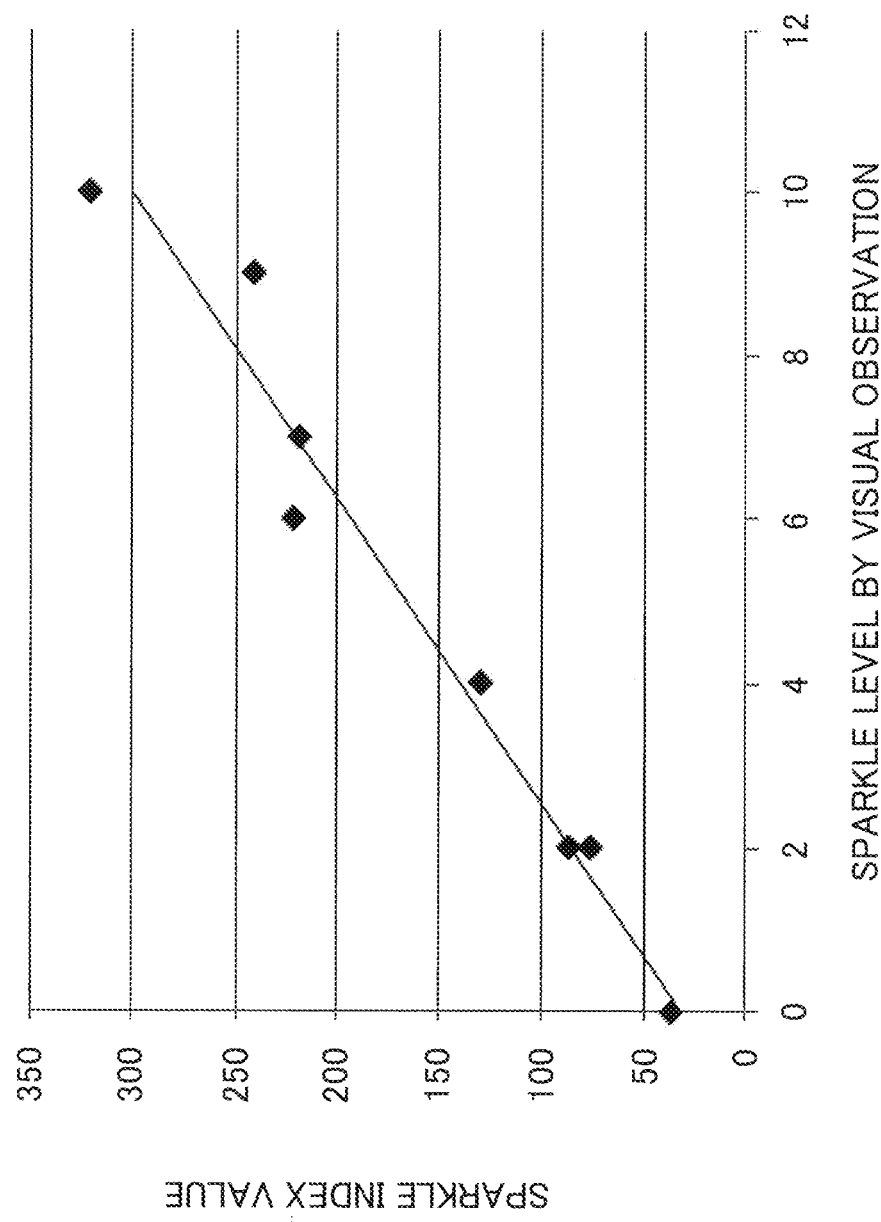
FIG. 13 is a graph showing an example of a relationship between the sparkle index value (a vertical axis) and the level of the sparkle by a visual observation (a horizontal axis) that is obtained for each transparent substrate.

FIG. 13 shows an example of a relationship between the sparkle index value (the vertical axis) and the level of the sparkle by the visual observation.

From FIG. 13, it can be seen that there is a positive correlation between them.

This result indicates that the sparkle index value corresponds a result of the determination of the sparkle through the visual observation by the observer, and therefore suggests that the sparkle of the transparent substrate can be evaluated by using the sparkle index value. In other words, it can be said that, by using the sparkle index value, the sparkle of the transparent substrate can be objectively and quantitatively determined.

In this manner, it has been verified that the resolution index value T, the reflection image diffusiveness index value R, and the sparkle index value can be used as quantitative indexes of the resolution, the reflection image diffusiveness, and the anti-glare property of the transparent substrate, respectively.

The present invention can be utilized, for example, for evaluating optical characteristics of a transparent substrate that is installed in various types of display devices, such as an LCD device, an OLED device, a PDP device, and a tablet type display device. Further, the present application is based on and claims the benefit of priority of Japanese Patent Application No. 2013-030238 filed on Feb. 19, 2013, the entire contents of which are herein incorporated by reference.

What is claimed is:

1. A method of evaluating optical characteristics of a transparent substrate that is disposed on a display device, comprising:

selecting two values among a quantified resolution index value, a quantified reflection image diffusiveness index value, and a quantified sparkle index value of the transparent substrate, wherein the quantified resolution index value is obtained by irradiating a first light beam from a side of a second surface of the transparent substrate having a first surface and the second surface in a direction that is parallel to a thickness direction of the transparent substrate, measuring brightness of a transmitted beam, which is referred to as 0° transmitted light beam, that transmits in a direction that is parallel to the thickness direction of the transparent substrate from the first surface, varying a reception angle of the first light beam with respect to the first surface of the transparent substrate in a range from −90° to +90°, measuring brightness of all transmitted beams that are transmitted from a side of the first surface, and calculating the resolution index value T from expression (1), the resolution index value T=(the brightness of all the transmitted beams−the brightness of the 0° transmitted light beam)/the brightness of all the transmitted beams, the quantified reflection image diffusiveness index value is obtained by irradiating a second light beam from the side of the first surface of the transparent substrate having the first surface and the second surface in a direction that is 45° with respect to the thickness of the transparent substrate, measuring brightness of a 45° regular reflected beam that reflects on the first surface, measuring brightness of all reflected beams that are reflected by the first surface by varying a light reception angle of receiving the reflected beam that is reflected by the first surface in a range from 0° to +90°, and calculating the reflection image diffusiveness index value R from expression (2), the reflection image diffusiveness index value R=(the brightness of all the reflected beams−the brightness of the 45° regular reflected beam)/the brightness of all the reflected beams, and the quantified sparkle index value is obtained by disposing the transparent substrate that has the first surface and the second surface on the display device such that the second surface is at a side of the display device, taking a photograph of the transparent substrate from the side of the first surface and obtaining a digital image, selecting a part of the digital image as an analysis area, dividing the analysis area into a plurality of areas that are formed of a plurality of pixels, obtaining, for each of the areas, the maximum brightness value and the maximum brightness gradient, and quantifying the sparkle of the transparent substrate by using an index value that is calculated from variations of the maximum brightness values and the maximum brightness gradients, respectively, in the analysis area.

2. The method according to claim 1, wherein a combination of the selected index values is a combination of the resolution index value and the reflection image diffusiveness index value, a combination of the sparkle index value and the reflection image diffusiveness index value, or a combination of the resolution index value and the sparkle index value.

3. The method according to claim 2, wherein the resolution index value and/or the reflection image diffusiveness index value is obtained by using a goniometer.

4. The method according to claim 2, wherein the display device is one of a LCD device, an OLED device, a PDP device, and a tablet type display device.

5. The method according to claim 2, wherein the transparent substrate is formed of soda-lime glass or aluminosilicate glass.

6. The method according to claim 5, wherein a chemically strengthening process is applied to at least one of the first surface and the second surface of the transparent substrate.

7. The method according to claim 2, wherein an anti-glare process is applied to the first surface.

8. The method according to claim 7, wherein the anti-glare process is implemented by applying at least one processing method on the first surface of the transparent substrate, wherein the at least one processing method is selected from a group including a frost process, an etching process, a sandblast process, a lapping process, and a silica-coating process.

9. The method according to claim 1, wherein the resolution index value and/or the reflection image diffusiveness index value is obtained by using a goniometer.

10. The method according to claim 9, wherein the transparent substrate is formed of soda-lime glass or aluminosilicate glass.

11. The method according to claim 9, wherein an anti-glare process is applied to the first surface.

12. The method according to claim 1, wherein the display device is one of a LCD device, an OLED device, a PDP device, and a tablet type display device.

13. The method according to claim 1, wherein the transparent substrate is formed of soda-lime glass or aluminosilicate glass.

14. The method according to claim 13, wherein a chemically strengthening process is applied to at least one of the first surface and the second surface of the transparent substrate.

15. The method according to claim 14, wherein an anti-glare process is applied to the first surface.

16. The method according to claim 15, wherein the anti-glare process is implemented by applying at least one processing method on the first surface of the transparent substrate, wherein the at least one processing method is selected from a group including a frost process, an etching process, a sandblast process, a lapping process, and a silica-coating process.

17. The method according to claim 13, wherein an anti-glare process is applied to the first surface.

18. The method according to claim 17, wherein the anti-glare process is implemented by applying at least one processing method on the first surface of the transparent substrate, wherein the at least one processing method is selected from a group including a frost process, an etching process, a sandblast process, a lapping process, and a silica-coating process.

19. The method according to claim 1, wherein an anti-glare process is applied to the first surface.

20. The method according to claim 19, wherein the anti-glare process is implemented by applying at least one processing method on the first surface of the transparent substrate, wherein the at least one processing method is selected from a group including a frost process, an etching process, a sandblast process, a lapping process, and a silica-coating process.

* * * * *